United States Patent [19]

Venturello et al.

[11] Patent Number: 4,701,550
[45] Date of Patent: Oct. 20, 1987

[54] PROCESS FOR PREPARING ALKYL ESTERS OF METHYLTARTRONIC ACID

[75] Inventors: Carlo Venturello; Enzo Alneri; Alfredo Coassolo; Rino D'Aloisio, all of Novara, Italy

[73] Assignee: Istituto Guido Donegani S.p.A., Novara, Italy

[21] Appl. No.: 745,238

[22] Filed: Jun. 17, 1985

[30] Foreign Application Priority Data

Jun. 18, 1984 [IT] Italy ................. 21460 A/84

[51] Int. Cl.$^4$ ............................................. C07C 67/40
[52] U.S. Cl. ..................... 560/180; 562/525; 562/582; 562/587
[58] Field of Search ............... 560/180; 562/525, 587, 562/582

[56] References Cited

U.S. PATENT DOCUMENTS

| | | | |
|---|---|---|---|
| 2,006,314 | 6/1935 | Halbig et al. | 562/525 |
| 2,373,942 | 4/1945 | Bergsteinsson | 568/860 |
| 2,500,599 | 3/1950 | Bergsteinsson et al. | 562/587 |
| 2,613,223 | 10/1952 | Young | 562/587 |
| 2,731,502 | 1/1956 | Smith | 562/587 |
| 2,808,442 | 10/1957 | Smith et al. | 562/587 |

FOREIGN PATENT DOCUMENTS

| | | | |
|---|---|---|---|
| 0056264 | 7/1982 | European Pat. Off. | 560/180 |
| 2524222 | 1/1976 | Fed. Rep. of Germany | 560/180 |
| 3316264 | 11/1984 | Fed. Rep. of Germany | 560/180 |

OTHER PUBLICATIONS

Edamura et al, *Chemical Abstracts*, vol. 92, No. 6072w, (1980).
Mitsubishi, *Chemical Abstracts*, vol. 97, No. 91749t, (1982).
Kawamata et al, *Chemical Abstracts*, vol. 88, No. 136144z, (1978).

*Primary Examiner*—Donald B. Moyer
*Assistant Examiner*—Bruce D. Gray
*Attorney, Agent, or Firm*—Stevens, Davis, Miller & Mosher

[57] ABSTRACT

There is described a process for preparing alkyl esters of methyltartronic acid by hydroxylation of methacrylic acid to alpha-methylglyceric acid with $H_2O_2$, in an aqueous medium, in the presence of $H_2WO_4$ and optionally of $H_3PO_4$ or $H_3AsO_4$ or alkaline salts thereof as catalysts, at pH < 2 and at temperatures of from 50° to 100° C., by subsequent oxidation of alpha-methylglyceric acid to methyltartronic acid with $HNO_3$ in excess or with $O_2$, in an aqueous-alkaline medium, in the presence of Pd or Pt carried on carbon or oxides thereof as catalysts, at temperatures of 60°–100° C., and final esterification of methyltartronic acid with alcohols $C_1$–$C_4$.

5 Claims, No Drawings

PROCESS FOR PREPARING ALKYL ESTERS OF METHYLTARTRONIC ACID

The present invention relates to a process for preparing alkyl esters of methyltartronic acid starting from methacrylic acid.

BACKGROUND OF THE INVENTION

It is known how to prepare the ethyl ester of methyltartronic acid by oxidizing, with $HNO_3$ at 98% or with $KMnO_4$, in an alkaline environment, the ethyl methylmalonate.

According to other methods, the above said esters are generally prepared by hydrolysis of methyl-bromomalonic acid with barite water and by subsequent esterification with an alcohol, or by acid alcoholysis of alpha-cyanolactic acid (cyanohydrin of pyruvic acid) or of 2-acetoxy-2-methylmalonitrile (1-acetoxy-1,1-dicyanoethane).

None of these methods, however, proves satisfactory for a utilization on a commercial scale.

In fact, said methods involve the use of expensive and not easily available raw materials, such as methylmalonic acid or the ethyl ester thereof and the pyruvic acid, or provide very unsatisfactory yields, or require the use of toxic and hazardous-to-handle substances, such as hydrocyanic acid.

DESCRIPTION OF THE INVENTION

The objects of the present invention consist in obtaining, with high yields and selectivities, alkyl esters of methyltartronic acid, by means of a simple and economic process, using non-expensive, easily available and non-dangerous raw material and reagents.

It has now been found that the abovesaid objects are achieved by a process comprising the catalytic hydroxylation with hydrogen peroxide of the methacrylic acid to alpha-methylglyceric acid and the subsequent oxidation, with nitric acid or with oxygen in the presence of catalysts, or the alpha-methylglyceric acid to methyltartronic acid, which is at last esterified with alcohols.

Thus, it is an object of the present invention to provide a process for preparing alkyl esters, having from 1 to 4 carbon atoms, of the methyltartronic acid, comprising the steps of:

(a) reacting the methacrylic acid with hydrogen peroxide, in an aqueous medium, in the presence of a catalyst consisting of tungstic acid or of an alkaline salt thereof and optionally of phosphoric acid or arsenic or of an alkaline salt thereof, at pH values lower than 2 and at temperatures ranging from 50° to 100° C.;

(b) Subsequently reacting the alpha-methylglyceric acid, obtained in step (a), with an excess of nitric acid at least at a 40% concentration or with oxygen or air, in an aqueous solution of an inorganic base, in the presence of a catalyst consisting of palladium or platinum carried on carbon or of oxides thereof, at temperatures ranging from 60° to 100 ° C.; and (c) esterifying with alcohols, having from 1 to 4 carbon atoms, the methyltartronic acid obtained in step (b). The main reactions of the process according to the invention can be schematically represented as follows:

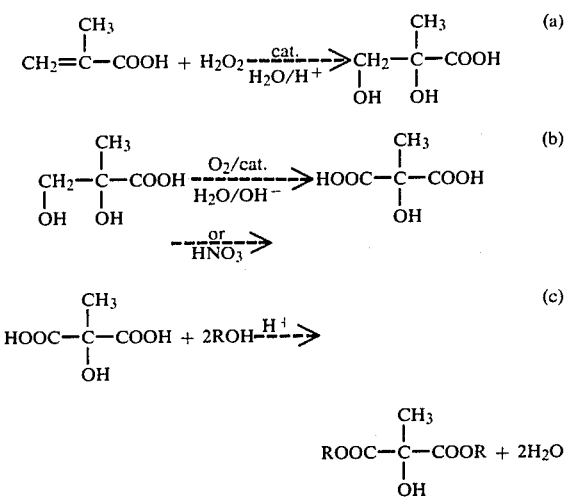

In step (a) there are employed methacrylic acid concentrations in the reaction mixture of 1-20% by weight, preferably of 5-10% by weight, and hydrogen peroxide concentrations of 1-8% by weight, preferably of 2-4% by weight, while the catalyst is employed in catalytic amounts, preferably in such amounts as to have from 0.01 to 0.02 gram -atoms of tungsten and optionally of phosphorus or arsenic per mole of methacrylic acid.

Methacrylic acid and hydrogen peroxide are employable in stoichiometric molar amounts, but it is preferable to employ a moderate excess of methacrylic acid of 10-12% with respect to the stoichiometric amount. In step (a) the methacrylic acid/$H_2O_2$ molar ratio employed can range from 1:1 to 1.1:1.

In step (b), in the case of oxidation with $O_2$ and catalysts, there are utilized concentrations of alpha-methylglyceric acid in the aqueous-alkaline medium ranging from 10 to 15% by weight, inorganic base/alpha-methylglyceric acid molar ratios ranging from 2.4 to 2.6, while the catalyst is utilized in catalytic amounts, preferably in such amounts as to have from 0.01 to 0.001 gram -atoms of palladium or of platinum per mole of alpha-methylglyceric acid.

According to an effective embodiment, it is practically operated as follows.

The methacrylic acid, the aqueous solution of hydrogen peroxide and the catalyst are introduced into a reactor equipped with a feed systems for the reagents, with a reflux cooler, with a stirrer and thermoregulated; the whole is heated to a temperature of 80° C. for times of 2.5-3 hours, which are sufficient to obtain almost quantitative conversions of $H_2O_2$ and alpha-methylglyceric yields of 80-85% with respect to the $H_2O_2$ charged.

At the end of the reaction, the reaction mixture is cooled down, whereafter the unreacted methacrylic acid and the alpha-methylglyceric acid which has formed are recovered by extracting, with an organic solvent, the aqueous solution and, respectively, the residue thereof.

Suitable solvents for the extraction are ethyl ether or isopropyl ether for the methacrylic acid, and ethyl acetate or acetonitrile or acetone for the alpha-methylglyceric acid.

The alpha-methylglyceric acid so separated is introduced again into the reactor along with aqueous solution strongly alkaline due to NaOH or KOH, and with the catalyst based on Pd or Pt, then it is heated to 60°-100° C. and at this temperature oxygen is bubbled into the mixture for the time necessary to obtain the desired conversion, for example for 24 hours.

After cooling, the methyltartronic acid which has formed is then separated, with yields of 70-75% referred to alpha-methylglyceric acid, by filtration of the reaction mixture, acidification of the aqueous filtrate with mineral acids and subsequent evaporation of said filtrate.

The methyltartronic acid is extracted from the residue by means of a proper alcohol having from 1 to 4 carbon atoms.

As an alternative, alpha-methylglyceric acid, prepared as described hereinbefore, is reacted in the reactor with an excess of nitric acid at 65%, at 80° C. for 2 hours.

After cooling, the nitric acid in excess is evaporated and methyltartronic acid is obtained with yields of from 50 to 65%.

Finally, methyltartronic acid is esterified according to conventional methods, for example by refluxing the alcoholic solution of methyltartronic acid with catalytic amounts of concentrated $H_2SO_4$, preferably equal to 1.5% by weight referred to methyltartronic acid, during 5 hours. At the end, the alcoholic solvent is evaporated and from the residue, by operating according to conventional techniques, the methyltartronic acid ester is recovered at a sufficient purity degree and with yields of 75-80% referred to the methyltartronic acid.

The process of the present invention, unlike the processes of the art, permits to obtain the methyltartronic acid esters with high yields and selectivities, by using not expensive, easily available and not dangerous reagents and by operating according to a simple and economic prodecure, which is suited to be adopted for commercial scale production.

The lower alkyl esters, having 1 to 4 carbon atoms, of methyltartronic acid are widely used, in the preparative organic chemistry, as useful intermediates for preparing aminoacids, barbituric, oxazolidine derivatives exerting a pesticide or analgesic action.

In particular, the ethyl ester of methyltartronic acid represents a useful intermediate for preparing N-(3,5-dichlorophenyl)-5-methyl-5-carboethoxy-1,3-oxazolidin-2,4-dione, which is an effective fungicide known as "Serinal".

The following examples are given to illustrate the present invention, without being however a limitation thereof.

EXAMPLE 1

A glass four-neck reactor, equipped with a mechanical stirrer, a thermometer and a reflux cooler, was charged with 0.5 g (2 m.moles) of $H_2WO_4$, 40 ml of $H_2O$ and 17 ml of $H_2O_2$ at 35% w./vol. (175 m.moles), then it was heated to 50°-60° C. till complete solubility.

1 ml of $H_3PO_4$ at 42.5% (4.3 m.moles), 225 ml of $H_2O$ and 17.2 g (200 m.moles) of methacrylic acid were then added.

The mixture was brought, under intense stirring, to 80° C. and maintained at such temperature during 2.5 hours. It was cooled down and the solution was extracted with ethyl ether.

By evaporation of the ethereal extract, previously dried on $Na_2SO_4$, there were recovered 2.25 g (26.2 m. moles) of methacrylic acid.

The residual aqueous solution, after elimination of unreacted $H_2O_2$, was evaporated to dryness and the residue was extracted with ethyl acetate at 40° C.

The extract was filtered to separate the insoluble salts, and the resulting filtrate, after drying on $Na_2SO_4$, was evaporated, thus providing 18.1 g of alpha-methylglyceric acid of sufficient purity.

The same reactor, which was equipped with a bubbler and whose cooler was connected with a bubble-counter, was charged with the alpha-methylglyceric acid obtained in the preceding step, with 15.2 g of NaOH, 150 ml of $H_2O$ and 2.4 g of palladium carried on carbon at 5%.

Oxygen was then bubbled thereinto and the solution was heated to 100° C. and kept at such temperature during 24 hours under intense stirring.

After such time, it was cooled, the catalyst was filtered and the filtrate was acidified with 20% HCl, until complete release of the acid, whereafter it was evaporated to dryness.

The residue repeatedly extracted with 400 ml of anhydrous ethyl alcohol.

The ethanol solution, containing 14.28 g of methyltartronic acid was added with 0.15 ml of $H_2SO_4$ at 96% and was refluxed during 5 hours. At the conclusion it was neutralized, was distilled off the ethyl alcohol and the residue was extracted with ether.

The ethereal extract was then dried on $Na_2SO_4$ and at last it was evaporated, thus providing 15.7 g of ethyl ester methyltartronic acid with a sufficient purity.

EXAMPLE 2

It was operated exactly as in example 1, till obtaining alpha-methylglyceric acid.

Into the same reactor there were introduced the obtained alpha-methyl-glyceric acid and 79.2 g of $HNO_3$ at 65% (0.82 moles), it was slowly heated to 80° C. and such temperature was maintained for 2 hours. Then the nitric acid was evaporated in a rotary evaporator while adding small amounts of benzene to facilitate the removal of the residual $HNO_3$.

There were obtained 13.27 g of methyltartronic acid of sufficient purity and having the appearance of a somewhat pasty white solid with a yield of 65.6% referred to alpha-methylglyceric acid.

The product obtained was dissolved in 400 ml of anhydrous ethyl alcohol and it was esterified with $H_2SO_4$ as in example 1, thus obtaining 14.59 g of ethyl ester of methyltartronic acid of sufficient purity.

We claim:

1. A method of preparing alkyl esters of methyltartronic acid, characterized in that:
   (a) methacrylic acid is reacted, at 50°-100° C., with hydrogen peroxide in an aqueous medium, in the presence of a catalyst selected from the group consisting of tungstic acid and alkali metal salts thereof at pH values lower than 2;
   (b) the thus obtained alpha-methyl-glyceric acid is oxidized, at 60°-100° C., in an aqueous solution of an inorganic base, by means of an oxidizing agent selected from the group consisting of concentrated nitric acid (at least 40% by weight), oxygen, and air, in the presence of a catalyst selected from the group consisting of palladium, platinum, and oxides thereof, carried on carbon; and
   (c) the thus obtained methyl-tartronic acid is esterified with an alkyl alcohol having from 1 to 4 C atoms.

2. The method according to claim 1 wherein the methacrylic acid: $H_2O_2$ molar ratio ranges from 1 to 1.1 and wherein the amount of tungstic acid and alkali metal salt thereof ranges from 0.01 to 0.02 mole per mole of methacrylic acid.

3. The process according to claim 2 in which the concentration of methacrylic acid in the reaction mixture ranges from 1 to 20% by weight and the concentration of $H_2O_2$ ranges from 1 to 8% by weight.

4. The process according to claim 1, in which in reaction step (b), in the case of oxidation with $O_2$ and catalysts, there are employed inorganic base/ alpha-methylglyceric acid molar ratios ranging from 2.4 to 2.6 and catalyst amounts, expressed as metal, ranging from 0.01 to 0.001 gramme-atoms per mole of alpha-methylglyceric acid.

5. The process according to claim 4, in which the concentration of alpha-methylglyceric acid in the basic aqueous solution ranges from 10 to 15% by weight and the inorganic base is sodium hydroxide or potassium hydroxide.

* * * * *